United States Patent
Foad et al.

(10) Patent No.: US 9,915,621 B2
(45) Date of Patent: Mar. 13, 2018

(54) EXTREME ULTRAVIOLET (EUV) SUBSTRATE INSPECTION SYSTEM WITH SIMPLIFIED OPTICS AND METHOD OF MANUFACTURING THEREOF

(71) Applicant: Applied Materials, Inc., Santa Clara, CA (US)

(72) Inventors: Majeed A. Foad, Sunnyvale, CA (US); Christopher Dennis Bencher, Cupertino, CA (US); Christopher G. Talbot, Emerald Hills, CA (US); John Christopher Moran, Menlo Park, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 0 days.

(21) Appl. No.: 15/031,690

(22) PCT Filed: Dec. 18, 2014

(86) PCT No.: PCT/US2014/071321
§ 371 (c)(1),
(2) Date: Apr. 22, 2016

(87) PCT Pub. No.: WO2015/095621
PCT Pub. Date: Jun. 25, 2015

(65) Prior Publication Data
US 2016/0282280 A1 Sep. 29, 2016

Related U.S. Application Data

(60) Provisional application No. 61/918,639, filed on Dec. 19, 2013.

(51) Int. Cl.
*G01N 21/95* (2006.01)
*G01N 21/956* (2006.01)

(52) U.S. Cl.
CPC .......... *G01N 21/95* (2013.01); *G01N 21/956* (2013.01); *G01N 2021/95676* (2013.01); *G01N 2201/061* (2013.01)

(58) Field of Classification Search
CPC ................ G01N 21/91; G01N 21/956; G01N 21/95676; G01J 1/04; G03F 1/22
See application file for complete search history.

(56) References Cited

U.S. PATENT DOCUMENTS 6,738,135 B1 5/2004 Underwood et al.
2011/0181868 A1* 7/2011 Stokowski ............ B82Y 10/00
356/51

(Continued)

FOREIGN PATENT DOCUMENTS

CN 103424985 A 12/2013
JP 2012118304 A 8/2011

OTHER PUBLICATIONS

PCT International Search Report and Written Opinion in PCT/US2014/071321 dated Mar. 26, 2015, 10 pages.

(Continued)

Primary Examiner — Casey Bryant
(74) Attorney, Agent, or Firm — Servilla Whitney LLC

(57) ABSTRACT

An extreme ultraviolet (EUV) substrate inspection system and method of manufacturing thereof, includes: an EUV source directing EUV illumination through an aperture; a light detector detecting mask illumination with reduced off axis rays reflected off from a substrate; and a computing device processing image data detected by the light detector.

12 Claims, 2 Drawing Sheets

(56) References Cited

U.S. PATENT DOCUMENTS

| | | | | |
|---|---|---|---|---|
| 2012/0008123 A1* | 1/2012 | Lee | ............... | B82Y 10/00 |
| | | | | 355/55 |
| 2012/0236281 A1* | 9/2012 | Wang | ............... | G03F 1/84 |
| | | | | 355/67 |
| 2013/0017475 A1* | 1/2013 | Terasawa | ............ | G01N 21/8806 |
| | | | | 430/5 |
| 2013/0056642 A1* | 3/2013 | Lee | ............... | B82Y 40/00 |
| | | | | 250/372 |
| 2013/0083321 A1* | 4/2013 | Wack | ............... | G03F 1/84 |
| | | | | 356/239.3 |

OTHER PUBLICATIONS

PCT International Preliminary Report on Patentability in PCT/US2014/071321 dated Jun. 21, 2016, 8 pages.

\* cited by examiner

EXTREME ULTRAVIOLET (EUV) SUBSTRATE INSPECTION SYSTEM WITH SIMPLIFIED OPTICS AND METHOD OF MANUFACTURING THEREOF

CROSS-REFERENCE TO RELATED APPLICATION(S)

This application claims the benefit of U.S. Provisional Patent Application Ser. No. 61/918,639 filed Dec. 19, 2013, and the subject matter thereof is incorporated herein by reference thereto.

TECHNICAL FIELD

The present invention relates generally to extreme ultraviolet lithography substrate review and inspection, and more particular to an extreme ultraviolet substrate inspection system with a simplified optics, and manufacturing thereof.

BACKGROUND

Extreme ultraviolet lithography, also known as soft x-ray projection lithography, is a contender to replace deep ultraviolet lithography for the manufacture of 0.13 micron, and smaller, minimum feature size semiconductor devices.

However, extreme ultraviolet light, which is generally in the 5 to 40 nanometer wavelength range, is strongly absorbed in virtually all materials. For that reason, extreme ultraviolet systems work by reflection rather than by transmission of light. Through the use of a series of mirrors, or lens elements, and a reflective element, or extreme ultraviolet substrates such as EUV mask blanks, coated with a non-reflective absorber mask pattern, the patterned actinic light is reflected onto a resist-coated semiconductor wafer.

The lens elements and extreme ultraviolet mask blanks of extreme ultraviolet lithography systems are coated with reflective multilayer coatings of materials such as molybdenum and silicon. Reflection values of approximately 65% per lens element, or EUV mask blank, have been obtained by using substrates that are coated with multilayer coatings that strongly reflect light essentially at a single wavelength within an extremely narrow ultraviolet bandpass; e.g., 12 to 14 nanometer bandpass for 13 nanometer ultraviolet light.

Minimum feature size design rules for semiconductor and microelectronics manufacturing continue to shrink with Moore's Law. Use of short wavelength, extreme ultraviolet lithography has the potential to facilitate even smaller design rules although many technical challenges remain to fully commercialize this technology. High-quality, defect-free masks are one critical link the chain. Mask defect inspection generally is expensive and complex.

Thus, a need still remains for an extreme ultraviolet lithography substrate inspection system with simplified optics. In view of growing demands for supporting high-quality and defect-free masks, it is increasingly critical that answers be found to these problems. In view of the ever-increasing commercial competitive pressures, along with growing consumer expectations and the diminishing opportunities for meaningful product differentiation in the marketplace, it is critical that answers be found for these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

SUMMARY OF THE INVENTION

Embodiments of the present invention provide an extreme ultraviolet (EUV) substrate inspection system includes: an EUV source directing EUV illumination through an aperture; a light detector detecting mask illumination with reduced off axis rays reflected off from a substrate; and a computing device processing image data detected by the light detector.

Embodiments of the present invention provide a method of manufacturing of an EUV substrate inspection system includes: providing an EUV source; directing EUV illumination of the EUV source onto a substrate through an aperture; detecting mask illumination with reduced off axis rays reflected off from the substrate onto a light detector; transferring image data from the light detector to a computing device; and processing the image data on the computing device.

Embodiments of the present invention provide a device of an EUV point source includes: an EUV source directing EUV illumination through an aperture; and a light detector having the aperture, the light detector detecting mask illumination with reduced off axis rays.

Certain embodiments of the current invention have other steps or elements in addition to or in place of those mentioned above. The steps or element will become apparent to those skilled in the art from a reading of the following detailed description when taken with reference to the accompanying drawings.

DETAILED DESCRIPTION

Figure 1:
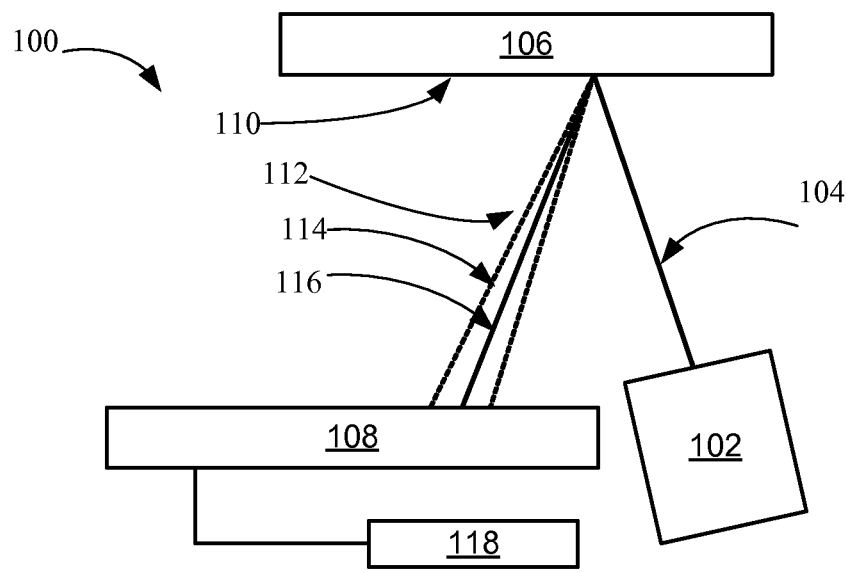
FIG. 1 is an exemplary of an EUV substrate inspection system in a first embodiment of the present invention.

The following embodiments are described in sufficient detail to enable those skilled in the art to make and use the invention. It is to be understood that other embodiments would be evident based on the present disclosure, and that system, process, or mechanical changes may be made without departing from the scope of the embodiments of the present invention.

In the following description, numerous specific details are given to provide a thorough understanding of the invention. However, it will be apparent that the invention may be practiced without these specific details. In order to avoid obscuring the embodiments of the present invention, some well-known circuits, system configurations, and process steps are not disclosed in detail.

The drawings showing embodiments of the system are semi-diagrammatic and not to scale and, particularly, some of the dimensions are for the clarity of presentation and are shown exaggerated in the drawing FIGs. Similarly, although the views in the drawings for ease of description generally show similar orientations, this depiction in the FIGs. is arbitrary for the most part. Generally, the invention can be operated in any orientation.

Where multiple embodiments are disclosed and described having some features in common, for clarity and ease of illustration, description, and comprehension thereof, similar and like features will be described with similar reference numerals.

For expository purposes, the term "horizontal" as used herein is defined as a plane parallel to the plane or surface of an extreme ultraviolet (EUV) mask, regardless of its orientation. The term "vertical" refers to a direction perpendicular to the horizontal as just defined. Terms, such as "above", "below", "bottom", "top", "side" (as in "sidewall"), "higher", "lower", "upper", "over", and "under", are defined with respect to the horizontal plane, as shown in the figures. The term "on" indicates that there is direct contact between elements.

The term "processing" as used herein includes deposition of material or photoresist, patterning, exposure, development, etching, cleaning, and/or removal of the material or photoresist as required in forming a described structure.

Embodiments of present invention provide a system and method of manufacturing of EUV substrate inspection. The system and method in accordance with the embodiments of the present invention may be used to inspect defects on reflective surfaces, such as EUV mask blanks, EUV masks, or wafers, with both high sensitivity, such as the ability to detect very small defects, and accuracy, such as the ability to reject background signals or blurring.

The EUV substrate inspection system and method of manufacturing in accordance with the embodiments of the present invention employ a "darkfield" or "brightfield" imaging technique. In the brightfield imaging technique, EUV illumination is directed onto the reflective surfaces. Reflected illumination, such as mask illumination reflected off from the reflective surfaces and detected by a light detector, is transmitted white light. The mask illumination is contrast caused by absorbance of some of the transmitted illumination in defects of the reflective surfaces. The typical appearance of the brightfield imaging technique in the EUV substrate inspection system is dark defects on a bright background.

By such the darkfield imaging technique, the mask illumination reflected off from the reflective surfaces is transmitted light that is not be detected by the light detector, and thus does not form part of the image. The darkfield imaging technique produces the classic appearance of a dark, almost black, background with bright defects thereon.

In accordance with the embodiments of the present invention, an EUV mask, or other reflective surfaces to be inspected, is coated with a layer of photoresist which is applied over areas of the EUV mask that are free of defects. The EUV mask is then exposed to the EUV illumination for a sufficient time to fully expose for developing the photoresist. The photoresist layer is fully exposed with a sufficient intensity and duration, for complete development and removal if there is no defect in the EUV mask.

When the EUV mask is perfect, no photoresist is left on the EUV mask surface after development. If, however, the EUV mask has defects, the areas immediately above and surrounding the defects on the EUV mask surface receive less exposure by reflection, and are not fully developed and removed. The defects may be easily detected by the remaining photoresist on the EUV mask surface after the development.

The EUV mask can be fabricated on bases such as glass, ceramic, silicon, or metallic materials. Silicon base can be of materials such as high density plasma (HDP) oxide, boron doped phosphorous glass, amorphous silicon. Metallic base can be of such metals as molybdenum, titanium, ruthenium, and their oxides or alloys. Thickness of the EUV mask can be various, including equal to or less than one millimeter (mm). The EUV mask can be configured to various dimensions and shapes including a square, a circular, or another shape in accordance to the design and requirement of the EUV substrate inspection system. Protection layers, reflective layers, or absorber layers can be built up over the base of the EUV mask. Patterns can be configured in the absorber layers.

An optical microscope, such as a darkfield microscope or a brightfield microscope, is sufficient to detect the remaining photoresist, or the defects, on the surface of the EUV mask or other reflective surfaces.

The microscope can include a series of reflecting mirrors and a pinhole camera, which is a simple camera without a lens but having a single small pinhole of a light-proof box. Light passes through the pinhole and projects an inverted image of a portion of the EUV mask on a screen opposite to a light source. By inspecting the inverted image of the EUV mask, the defects of the EUV mask can be detected and located.

For the EUV substrate inspection system using a pinhole camera, the resolution of the inverted image is based on the size of the pinhole, and the magnification is based on the ratio of an object distance which is a distance from an object to the pinhole, to an image distance which is a distance from the invented image to the pinhole. Up to a certain point, the smaller the pinhole, the sharper and dimmer the inverted image.

Because the pinhole camera requires a lengthy exposure, the EUV substrate inspection system using the pinhole camera scans slowly for the photoresist to expose adequately, resulting a slow scanning and a long inspection cycle. To expedite the inspection, an EUV substrate inspection system without the pinhole camera is developed.

The EUV substrate inspection system without the pinhole camera can include the light source, such as an EUV point source directing the EUV illumination onto the EUV mask. The light detector, such as an EUV image sensor, detects the mask illumination reflected off from the EUV mask, and transfers image data, such as image sensor data, to a computing device, such as an image processor to detect defects of the EUV mask and produce location information thereof.

The EUV point source produces the EUV illumination by suitable means including but not limited to laser-produced or discharge-produced plasma, synchrotron radiation, electric discharge sources, high-harmonic generation with femtosecond laser pulses, discharge-pumped x-ray lasers, or electron-beam driven radiation devices.

The EUV illumination, which is generally in the 5 to 40 nanometer (nm) wavelength range, is directed onto the EUV mask surface. The reflected illumination, such as mask blank illumination reflected off the EUV mask, can be detected by the EUV image sensor. The mask illumination projects image data, such as the image sensor data of the EUV mask and the defects thereof on the EUV image sensor. The EUV image sensor transfers the image sensor data to the image processor. The image processor utilizes various algorithms and techniques to eliminate image background noise and locate the defects of the EUV mask.

To obtain high sensitivity and accuracy of the EUV substrate inspection system, the mask illumination needs to be sufficiently focused and contrast. Blurring images caused by off axis rays of the mask illumination can prevent imaging or defects detection.

The EUV point source with an aperture or directed beam, can reduce the off axis rays resulting in image blurring reduction. Focused and contrast mask illumination with reduced off axis rays, can project sharp images and detect small defects of the EUV mask. Reduction of the off axis rays can be various in accordance with factors, such as the light source and the reflective surfaces. Normally, the reduction can be approximately 50% or greater comparing with the EUV point source without the aperture or directed beam. The EUV point source with reduced off axis rays can achieve a sub-20 nm or better resolution of the EUV mask.

It has been discovered that EUV point source with an aperture or direct beam can reduce the off axis rays approximately 50% or more, resulting in improving sensitivity and accuracy of the EUV substrate inspection system.

The EUV point source with the aperture can include an EUV point source, an aperture, and a condenser. The condenser is a lens that serves to concentrate the EUV illumination of the EUV point source. The EUV illumination enters the aperture, which allows an outer ring of the EUV illumination pass through. The condenser focuses the outer ring of the EUV illumination. The focused EUV illumination is directed onto the EUV mask surface. The EUV image sensor detects the mask illumination reflected off from the EUV mask surface, and transfers the image sensor data to the image processor to be processed.

The EUV substrate inspection system with the aperture and condenser is a complex structure and can increases manufacturing cost. An EUV point source with a simplified optics utilizes a through aperture of the EUV image sensor to replace the aperture and condenser. The EUV illumination is concentrated by the through aperture of the EUV image sensor before being directed onto the EUV mask surface to reduce the off axis rays up to 50% or more.

The EUV illumination is directed onto the EUV mask surface and reflected off from the EUV mask. The EUV image sensor can detect the mask illumination with reduced off axis rays bounced off from the EUV mask surface, including the images of the EUV mask and defects thereof. The blurring of the images can be improved because of the reduction of the off axis rays. The EUV image sensor can transfer the image sensor data to the image processor, for detecting the EUV mask defects and the locations thereof using various algorithms and techniques. Sharper images can enhance the sensitivity and accuracy of the substrate inspection system.

The detected image sensor data can include brightfield data and darkfield data. The EUV point source of the darkfield application can be at a glancing angle farther away from the EUV mask than the brightfield application. A typical distance from the EUV point source to the EUV mask is various depending on the applications and the equipment. For example, the distance from the EUV image sensor to the EUV mask can be approximately two to three meters. By adjusting the distance between the EUV image sensor and the EUV mask, the EUV light source that directs a beam of light to the EUV mask, the EUV image sensor can be positioned to record the reflection from a relatively large area of the EUV mask in a single exposure. The size and position of the EUV light source, as well as the size and position of the EUV image sensor, determine the illumination area on the EUV mask and the area that can be inspected.

The dimension of the through aperture of the EUV image sensor is determined by the formula $$d=\sqrt{2f\lambda}$$

where d is the aperture diameter, f is focal length (distance from the aperture to the EUV mask), and $\lambda$ is the wavelength of the EUV illumination.

The EUV image sensor can include a time delay and integration (TDI) sensor synchronized to a mask scan. TDI is a method of line scanning which provides dramatically increased responsivity compared to other video scanning methods. It permits much greater scanning speeds in low light, or allows reduced lighting levels and costs at conventional speeds. The improvement of the scanning speed depends on various factors, for example, image resolution, computing device capacity, scanner operating speed, or a combinational thereof. A typical scanning speed of the EUV image sensor with TDI can be two times or higher of the conventional speed.

The EUV mask inspection system can include a plurality of the EUV point sources. Multiple EUV point sources can scan the EUV mask in parallel to improve scanning efficiency. The EUV mask inspection system can inspect multiple areas of the EUV mask simultaneously, and the image processor can process the image sensor data of the multiple areas in parallel.

The surface of the EUV mask is parallel with the EUV image sensor. The EUV point source can direct the EUV illumination onto the EUV mask at an illumination angle, which is an oblique angle at the surface of the EUV image sensor. The through aperture of the EUV image sensor is formed through the EUV image sensor at an aperture angle at the surface of the EUV image sensor. The illumination angle usually is identical with the aperture angle, allowing the EUV illumination traveling through without any obstacle. The aperture angle can be various to be complied with the requirements of the substrate inspection system.

Diffraction may occur when the EUV illumination travels through the through aperture of the EUV image sensor. The diffraction phenomenon is described as the interference of waves when a wave encounters an obstacle or a slit that is comparable in size to illumination's wavelength. When the dimension of the through aperture is roughly comparable to the wavelength of the EUV illumination, diffraction patterns can be observed.

The image processor can utilize Ptychographic imaging technique along with advances of the EUV image sensor and the image processor computing to process the diffraction patterns, resulting in the optical microscopy with increased spatial resolution without the need for lens. Single or multiple diffraction patterns can be used to detect or extract images using Ptychography technique. Ptychography is a technique that aims to solve the diffraction pattern phase problem by interfering adjacent Bragg reflections coherently and thereby determine their relative phase. Bragg reflections give the angles for coherent and incoherent scattering, or forced illumination deviation, from a crystal lattice.

It has been discovered that detecting defects of substrates and extract location information of the defects are very important in the semiconductor manufacturing. Because of the difficulty to manufacture perfect substrates, the detection and location of the defects are essential. The imperfect substrate may contain numerous defects. The quality of the substrate can be acceptable as long as the number of the defects is under the manufacture's standard. During the manufacturing process, the dies where the defects are located can be discarded. In the meanwhile, the dies have no defects can be processed. The acceptable numbers of defects are various depending on the manufactures.

Referring now to FIG. 1, therein is shown an exemplary of an EUV substrate inspection system 100 in a first embodiment of the present invention. The brightfield point source substrate inspection system 100 can include an EUV point source 102 providing an EUV illumination 104, a substrate, such as an EUV mask 106, and a light detector, such as an EUV image sensor 108. The term "brightfield" is derived from the EUV image sensor 108 detecting a dark EUV mask on a bright background.

The EUV point source 102 produces the EUV illumination 104 by suitable means including but not limited to laser-produced or discharge-produced plasma, synchrotron radiation, electric discharge sources, high-harmonic generation with femto-second laser pulses, discharge-pumped x-ray lasers, or electron-beam driven radiation devices. The EUV illumination is generally in the 5 to 40 nanometer (nm) wavelength ranges.

The EUV point source 102 can direct the EUV illumination 104 onto a surface 110 of the EUV mask 106 at an oblique angle. The EUV mask is the reflective substrate configuring patterns to be printed on semiconductor wafers, typically on a photoresist layer. Distance from the EUV point source 102 to the surface 110 can be adjusted, in accordance with the application of a brightfield or darkfield. The EUV illumination 104 can uniformly illuminate a portion of the EUV mask 106 which is subjected to inspection. By moving the EUV mask 106 passing the EUV point source 102, the surface 110 of the EUV mask 106 can be scanned portion by portion.

When the EUV illumination 104 is directed on the surface 110, mask illumination 112 is reflected off from the EUV mask 106, projecting images onto the EUV image sensor 108. The mask illumination 112 can include off axis rays 114, which is diverted illumination from a center axis 116. The mask illumination 112 is contrast because of absorbance of some of the transmitted illumination by the EUV mask 106 and the defects thereof. The off axis rays 114 can cause blurring of the images projected onto the EUV image sensor 108, and degrade the defect detection.

The EUV image sensor 108 detects the mask illumination 112 and transfers the detected image sensor data to an image processor 118 for processing. The image processor 118 can utilize various algorithms and techniques to detect defects and process locations thereof. For example, a small defect on the surface 110 can have an image with blurring edge due to the off axis rays 114. The blurring image edges may be blended into the image background, resulting in that the image processor 118 fails to detect the defect.

Multiple EUV point sources can be utilized in illuminating multiple areas of the EUV mask 106 concurrently. The image processor 118 can process the image sensor data of the multiple areas in parallel. A TDI sensor can be included in the EUV image sensor 108. A darkfield substrate inspection system can be implemented in a similar structure with appropriate adjustment.

The brightfield point source substrate inspection system 100 shown in FIG. 1 is exemplary. The brightfield point source substrate inspection system 100 can include a series of mirrors or lens elements, such as facet mirrors or projection optics, which are not shown in FIG. 1.

It has been found that a brightfield point source substrate inspection system can expedite the scanning process by decreasing the exposure duration. Multiple EUV point sources can scan the substrate concurrently to improve the efficiency of the system.

Figure 2:
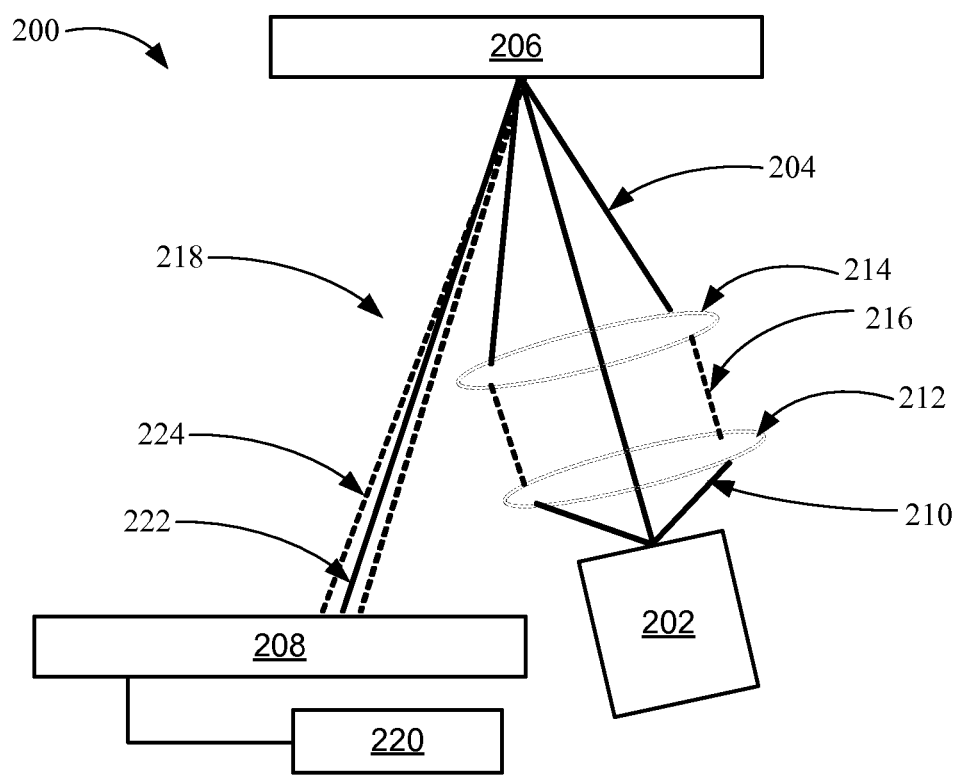
FIG. 2 is an exemplary of a focused EUV substrate inspection system in a second embodiment of the present invention.

Referring now to FIG. 2, therein is shown an exemplary of a focused EUV substrate inspection system 200 in a second embodiment of the present invention. The focused brightfield point source substrate inspection system 200 can include an EUV point source 202, focused EUV illumination 204, an EUV mask 206, and an EUV image sensor 208. The EUV point source 202 provides EUV illumination 210 passing through an aperture 212 and a condenser 214.

The EUV illumination 210 enters the aperture 212, which allows an outer ring 216 of the EUV illumination 210 pass through. The condenser 214 is a lens that serves to concentrate the outer ring 216 onto the EUV mask 206. The focused EUV illumination 204 is directed onto the EUV mask 206 at an oblique angle. Mask illumination 218 is reflected off from the EUV mask 206, and projects images of the EUV mask 206 and the defect thereof on the EUV image sensor 208. The mask illumination 218 is contrast because of absorbance of some of the transmitted illumination by the EUV mask 206 and the defects thereof.

The EUV image sensor 208 detects the mask illumination 218 and transfers the detected image sensor data to an image processor 220 to detect defects and process locations thereof. The mask illumination 218 has a center axis 222 and off axis rays 224. Compared with the mask illumination 112 of FIG. 1, the mask illumination 218 is more focused and has less off axis rays 224 to reduce image blurring. The focused brightfield point source substrate inspection system 200 can reduce image blurring. The reduction of the blurring can be various depending on dimension of the aperture 212 and the condenser 214, along with other conditions and restrictions.

Plurality of the EUV point source 202 with the aperture 212 and the condenser 214 can be utilized in illuminating multiple areas of the EUV mask 206 concurrently. The image processor 220 can process the image sensor data of the multiple areas in parallel. A TDI sensor can be included in the EUV image sensor 208. A darkfield substrate inspection system can be implemented in a similar structure with appropriate adjustment.

The focused brightfield point source substrate inspection system 200 shown in FIG. 2 is exemplary. The focused brightfield point source substrate inspection system 200 can include a series of mirrors or lens elements, such as facet mirrors or projection optics, which are not shown in FIG. 2.

It has been found that a focused brightfield point source substrate inspection system with aperture and condenser reduces image blurring, resulting in improvement of accuracy and sensitivity of imaging and defect detection.

Figure 3:
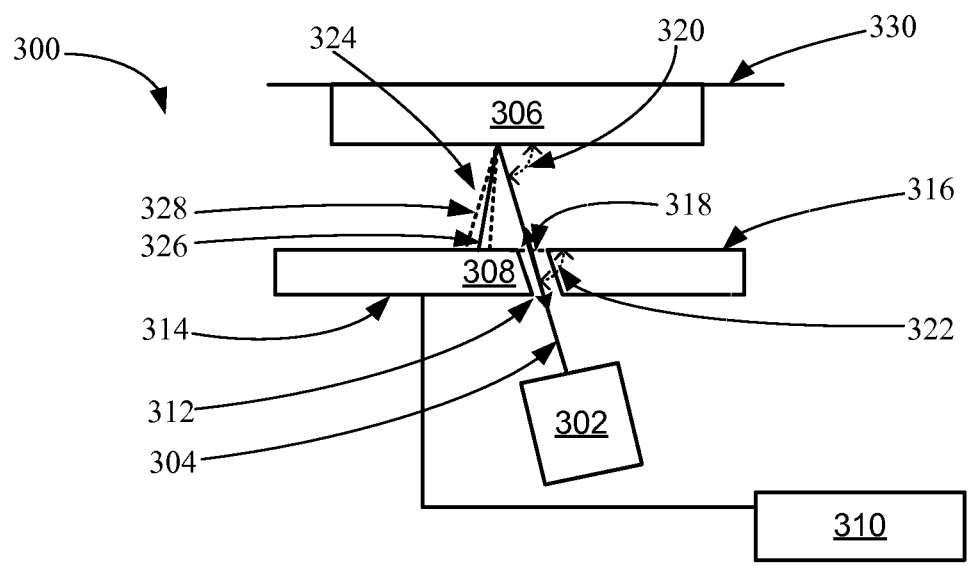
FIG. 3 is an exemplary of an EUV substrate inspection system with simplified optics in a third embodiment of the present invention.

Referring now to FIG. 3, therein is shown an exemplary of an EUV substrate inspection system 300 with simplified optics in a third embodiment of the present invention. The EUV substrate inspection system 300 with the simplified optics can include an EUV point source 302 providing EUV illumination 304, an EUV mask 306, an EUV image sensor 308, and an image processor 310.

The focused brightfield point source substrate inspection system 200 has a complex structure including the aperture 212 and the condenser 214 of FIG. 2, increasing the cost of manufacturing. The EUV substrate inspection system 300 with the simplified optics utilizes an aperture 312 of the EUV image sensor 308 to replace the aperture 212 and the condenser 214.

Formed through the EUV image sensor 308 at an oblique angle, the aperture 312 can be a slit, a hole, or other spaces through the entire thickness of the EUV image sensor 308.

The EUV illumination 304 enters the aperture 312 from a back surface 314 facing away from the EUV mask 306, and exits the EUV image sensor 308 from a front surface 316 facing toward the EUV mask 306. The EUV illumination 304 is focused or concentrated by the aperture 312 when travels through the EUV image sensor 308.

The aperture 312 can be various shapes having a center 318, and a uniformed dimension through the EUV image sensor 308. The sidewall or sidewalls of the aperture 312 are parallel to the center 318. The EUV illumination 304 is directed onto the EUV mask 306 through the aperture 312 at an illumination angle 320, and illuminates a portion of the EUV mask uniformly. The center 318 of the aperture 312 forms an aperture angle 322 at the front surface 316, wherein the aperture angle 322 is identical to the illumination angle 320. Mask illumination 324 is reflected off from the EUV mask 306 and projects images of the EUV mask 306 and defects thereof on the EUV image sensor 308. The mask illumination 324 is contrast because of absorbance of some of the transmitted illumination by the EUV mask 306 and the defects thereof.

The EUV image sensor 308 detects the mask illumination 324 and transfers the detected image sensor data to the image processor 310, to detect defects and process locations thereof. The mask illumination 324 has a center axis 326 and off axis rays 328. Compared with the mask illumination 112 of FIG. 1, the mask illumination 324 has less off axis rays 328 resulting in reduction of image blurring. The reduction of the image blurring can be various depending on dimension and shape of the aperture 312 and the thickness of the EUV image sensor 308, along with other conditions and restrictions.

The EUV mask 306 can be mounted on a moveable stage 330. The moveable stage 330 can adjust position of the EUV mask 306 in both X and Y coordinates, with respect to positions of the EUV image sensor 308 and the EUV point source 302. The position of the EUV mask 306 can be adjusted in a plane parallel to the front surface 316. Entire surface of the EUV mask 306 can be scanned by the EUV point source 302, when the EUV mask 306 passing through the stationary EUV image sensor 308 and the EUV point source 302. The EUV image sensor 308 detects the mask illumination 324 during scanning, permitting the detection of defects of the entire EUV mask 306.

Diffraction may occur when the EUV illumination 304 travels through the aperture 312, when the dimension of the aperture 312 is comparable in size to wavelength of the EUV illumination 304. Diffraction phenomenon is described as interference of waves when a wave encounters an obstacle or a slit, such as the aperture 312. The diffraction patterns are images of the interference of waves, such as the interference of the EUV illumination 304. The mask illumination 324 can include the reflected EUV illumination 304, and the reflected diffraction patterns.

The EUV image sensor 308 detects the mask illumination 324, and transfers detected image sensor data to the image processor 310, for detecting the defects of the EUV mask 306 and processes locations thereof. The image sensor data can include brightfield data, darkfield data, or diffraction patterns.

Plurality of the EUV point source 302 can be used in the EUV substrate inspection system 300. Plurality of the EUV illumination 304 can illuminate multiple areas on the EUV mask 306 simultaneously, through plurality of the aperture 312. The image processor 310 can process the image sensor data detected from the multiple areas of the EUV mask 306 in parallel. A TDI sensor can be included in the EUV image sensor 308.

The EUV substrate inspection system 300 shown in FIG. 3 is exemplary. The EUV substrate inspection system 300 can include a series of mirrors or lens elements, such as facet mirrors or projection optics, which are not shown in FIG. 3.

It has been found that an EUV substrate inspection system with multiple EUV point sources can improve efficiency of the EUV mask scanning and reduce inspection cycle time dramatically.

The EUV substrate inspection system 300 can be utilized in darkfield and brightfield applications, in a similar structure with appropriate adjustments. Brightfield data can be sensed from a direct reflection point of the EUV mask 306, while darkfield data is sensed elsewhere. The darkfield data is obtained from light that is around the light from the direct reflection point. The term "darkfield" is derived from the EUV image sensor detecting a bright EUV mask on a dark background. The distance from the EUV point source 302 to the EUV mask 306 in darkfield application is farther than in brightfield application.

It has been found that, projecting EUV illumination of at least one EUV point source through at least one opening in an EUV image sensor, can significantly reduce off axis rays and improve image blurring and defect detection.

It has been further found that a single or multiple diffraction patterns generated by an aperture and detected by an EUV image sensor can be used to further improve imaging and defect detection by using ptychography technique.

The pychography technique aims to solve the diffraction pattern phase problem due to interfering adjacent Bragg reflections coherent by changing the phase, profile, or position of the illuminating beam. The technique has been found to increase spatial resolution to improve imaging.

Further, it has been found that an EUV image sensor can use a TDI sensor architecture that permits photoelectrons generated from multiple exposures to be summed with no additive noise to enable high-speed imaging under very low light conditions. The EUV image sensor with TDI can improve scanning speed and reduce substrate inspection cycle time.

Figure 4:
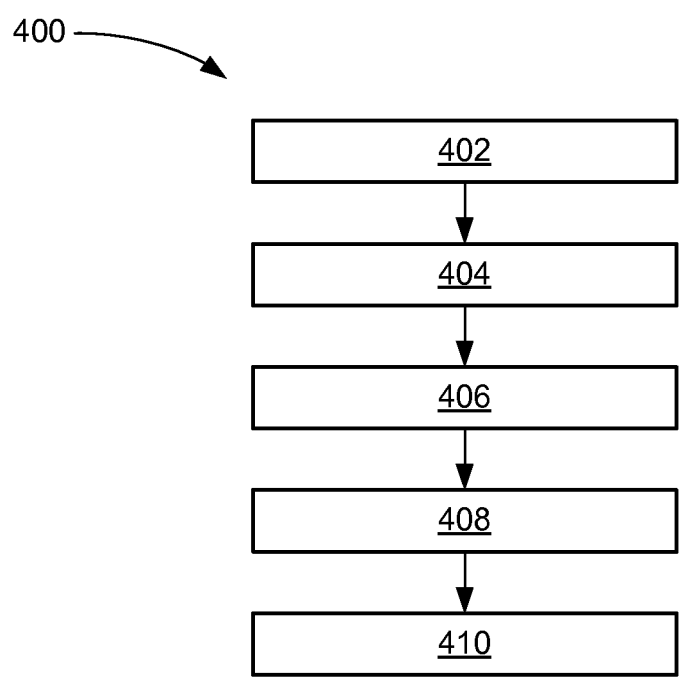
FIG. 4 is a flow chart of a method of manufacturing of the EUV substrate inspection system in a further embodiment of the present invention.

Referring now to FIG. 4, therein is shown a flow chart of a method 400 of manufacturing of the EUV substrate inspection system in a further embodiment of the present invention. The method 400 includes: providing an EUV source in a block of 402; directing EUV illumination of the EUV source onto a substrate through an aperture in a block of 404; detecting mask illumination with reduced off axis rays reflected off from the substrate onto a light detector in a block of 406; transferring image data from the light detector to a computing device in a block of 408; and processing the image data on the computing device in a block of 410.

The resulting method, process, apparatus, device, product, and/or system is straightforward, cost-effective, uncomplicated, highly versatile and effective, can be surprisingly and unobviously implemented by adapting known technologies, and are thus readily suited for efficiently and economically manufacturing an EUV substrate inspection system fully compatible with conventional manufacturing methods or processes and technologies.

Another important aspect of the embodiments of the present invention is that it valuably supports and services the historical trend of reducing costs, simplifying systems, and increasing performance.

These and other valuable aspects of the embodiments of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A method of operating an extreme ultraviolet (EUV) substrate inspection system comprising:
   providing an EUV source;
   directing EUV illumination of the EUV source onto a substrate through an aperture;
   reflecting the EUV illumination from the substrate to produce mask illumination having a center axis reflected from the substrate and off axis rays reflected from the substrate, the off axis rays being diverted from the center axis;
   detecting the mask illumination and image data with an EUV image sensor, wherein the aperture is through the EUV image sensor at an oblique angle;
   transferring image data from the EUV image sensor to a computing device, wherein transferring the image data from the EUV image sensor to the computing device includes transferring image sensor data of brightfield, darkfield, or diffraction patterns from the EUV image sensor to an image processor to locate defects of the substrate; and
   processing the image data on the computing device.

2. The method as claimed in claim 1, wherein providing the EUV source includes providing multiple EUV point sources.

3. The method as claimed in claim 1, wherein directing the EUV illumination of the EUV source through the aperture includes directing the EUV illumination of an EUV point source through the aperture of the EUV image sensor at an oblique angle onto a wafer, or an EUV mask.

4. The method as claimed in claim 1, wherein detecting the mask illumination with the EUV image sensor includes detecting the mask illumination onto the EUV image sensor with a plurality of apertures or a time delay and integration (TDI) sensor.

5. An EUV substrate inspection system comprising:
   an EUV source that can direct EUV illumination through an aperture onto an EUV substrate mounted on a stage to produce mask illumination having a center axis reflected from the EUV substrate and off axis rays reflected from the EUV substrate, the off axis rays being diverted from the center axis;
   an EUV image sensor that can detect the mask illumination and image data, wherein the aperture is through the EUV image sensor at an oblique angle; and
   a computing device that can process image data detected by the EUV image sensor, wherein the image data includes image sensor data of brightfield, darkfield, or diffraction patterns transferred from the EUV image sensor to an image processor, to locate defects of the substrate.

6. The system as claimed in claim 5, wherein the EUV source includes multiple EUV point sources.

7. The system as claimed in claim 5, wherein the EUV image sensor includes multiple apertures or a TDI sensor.

8. A device of an EUV point source comprising:
   an EUV point source that can direct EUV illumination through an aperture;
   an EUV image sensor that can detect image data and having the aperture through the EUV image sensor at an oblique angle; and
   a computing device that can process image data detected by the EUV image sensor, wherein the image data includes image sensor data of brightfield, darkfield, or diffraction patterns transferred from the EUV image sensor to an image processor to locate defects reflected from a substrate.

9. The device as claimed in claim 8, wherein the EUV point source include multiple EUV sources.

10. The device as claimed in claim 8, wherein the aperture includes a plurality of the apertures.

11. The device as claimed in claim 8, wherein the EUV image sensor includes a TDI sensor.

12. The device as claimed in claim 8, wherein the aperture through the EUV image sensor is at an oblique angle.

* * * * *